(12) United States Patent
Bucher

(10) Patent No.: US 7,927,006 B2
(45) Date of Patent: Apr. 19, 2011

(54) DEVICE FOR EXTRACTING, FRAGMENTING, MIXING AND HOMOGENIZING ESPECIALLY INFECTIOUS, MALODOROUS, CHEMICALLY CORROSIVE OR STERILE SUBSTANCES

(75) Inventor: Franz Gregor Bucher, Zug (CH)

(73) Assignee: Medic Tools AG, Zug (CH)

( * ) Notice: Subject to any disclaimer, the term of this patent is extended or adjusted under 35 U.S.C. 154(b) by 386 days.

(21) Appl. No.: 11/718,003

(22) PCT Filed: Nov. 18, 2005

(86) PCT No.: PCT/CH2005/000686
§ 371 (c)(1),
(2), (4) Date: Apr. 26, 2007

(87) PCT Pub. No.: WO2006/081694
PCT Pub. Date: Aug. 10, 2006

(65) Prior Publication Data
US 2009/0136384 A1    May 28, 2009

(30) Foreign Application Priority Data
Feb. 1, 2005  (CH) .......................... 146/05

(51) Int. Cl.
*B01L 3/00*      (2006.01)

(52) U.S. Cl. ....... 366/205; 422/258; 422/259; 241/82.1; 241/243; 241/246; 366/197; 366/199; 366/318; 366/343

(58) Field of Classification Search .................. 366/197, 366/199, 205, 318, 323, 343; 422/258, 259; 241/82.1, 243, 246
See application file for complete search history.

(56) References Cited

U.S. PATENT DOCUMENTS
4,767,069 A * 8/1988  Kim ............................ 241/152.2
7,490,976 B2 * 2/2009  Bucher ......................... 366/247

FOREIGN PATENT DOCUMENTS
| BE | 493035 | 12/1949 |
| CH | 366823 | 1/1963 |
| DE | 167144 | 1/1906 |
| FR | 2232365 | 1/1975 |
| FR | 2589754 | 5/1987 |
| WO | 2004035191 | 4/2004 |

* cited by examiner

*Primary Examiner* — Jill Warden
*Assistant Examiner* — Shogo Sasaki
(74) *Attorney, Agent, or Firm* — Volpe and Koenig, P.C.

(57) ABSTRACT

A device for extracting and fragmenting substances, especially infectious or malodorous substances, in a laboratory test vessel (3) is provided. The device includes a processing tool (11) and a stirrer element (33). An interior of the laboratory test vessel (3) is subdivided by a sieve (59) into a collection chamber and a processing chamber. The sieve (59) prevents parts of the substances having a defined rain size from reaching the collection chamber (73). A sample can be taken from the collection chamber using a pipette (45) which is passed through the stirrer element (33) and the sieve (59).

11 Claims, 2 Drawing Sheets

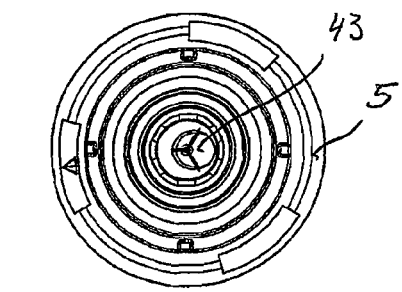
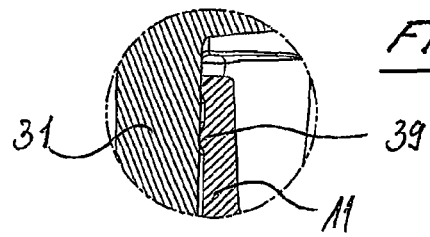
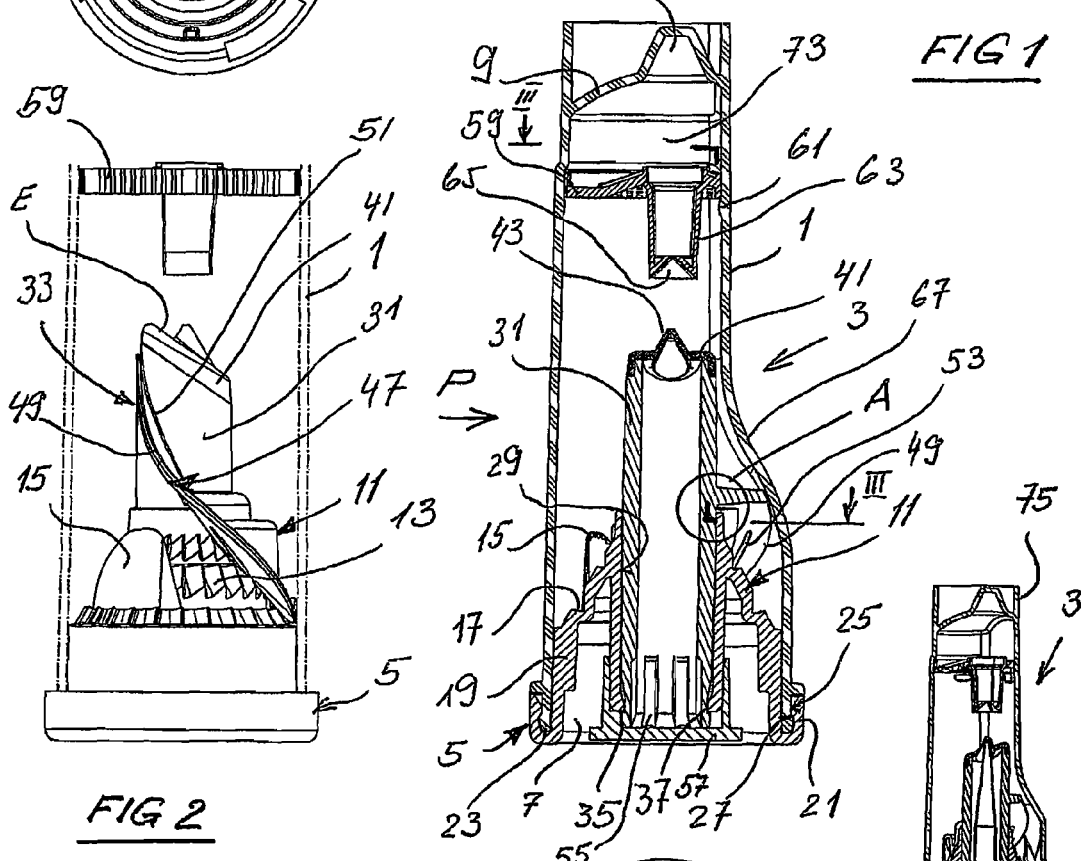
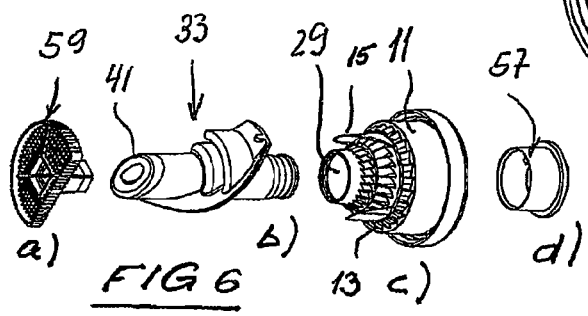
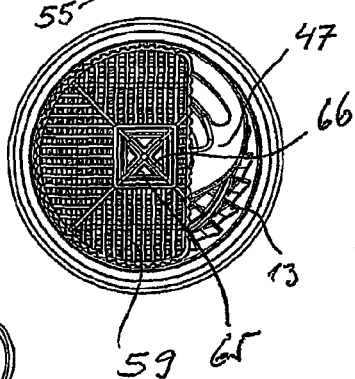

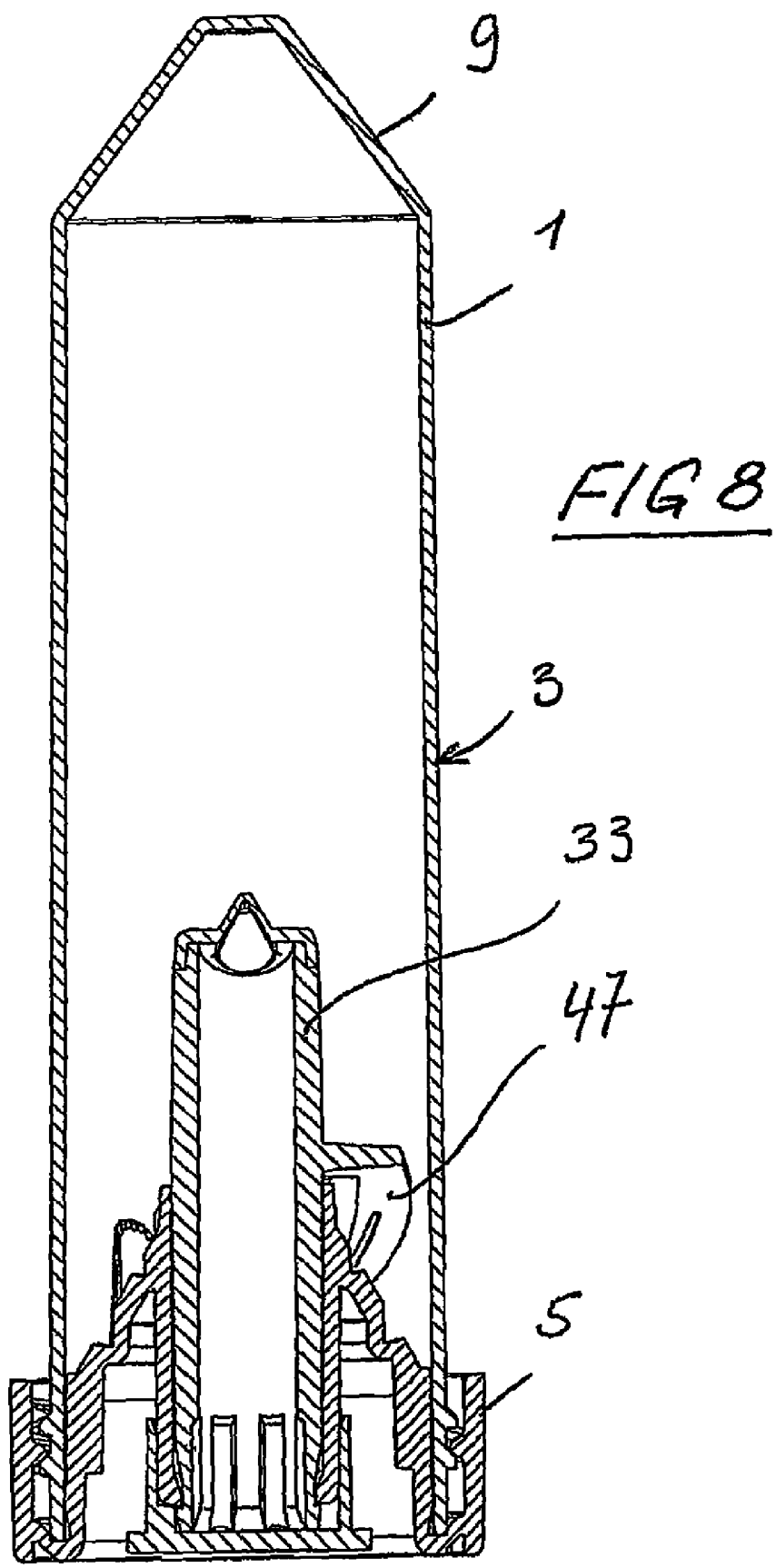

DEVICE FOR EXTRACTING, FRAGMENTING, MIXING AND HOMOGENIZING ESPECIALLY INFECTIOUS, MALODOROUS, CHEMICALLY CORROSIVE OR STERILE SUBSTANCES

BACKGROUND

The subject matter of the invention relates to a device for extracting, fragmenting, mixing, and homogenizing especially infectious, malodorous, chemically corrosive, or sterile substances according to the preamble of claim 1.

Devices of this type are known. From WO2004/035191 a one-way mixer and homogenizer is known, comprising a tubular laboratory test vessel, with an agitating element being supported for rotation in its lid having cutting and/or squeezing elements. At the periphery of the agitating element, connected in a torque-proof manner to the laboratory test vessel, cutting edges are formed at a retention sheath with the agitating element engaging them. Using this one-way mixer and homogenizer in particular infectious, malodorous, chemically corrosive, or sterile substances can be mixed and homogenized.

The substances processed inside the homogenization and mixing chamber remain hermetically isolated from the environment in this manner and, when the desired consistency has been reached, they can be removed via the shaft of the agitating element, which is hollow, without requiring the laboratory test vessel to be opened.

The disadvantage of this device is that when processing fibrous or chord-containing substances, the latter may clog the opening of the pipette for suctioning the processed sample and thus essentially hinder the removal of the test amount of the substance.

SUMMARY

The object of the present invention is to provide a device for extracting, fragmenting, mixing, and homogenizing in particular infectious, malodorous, chemically corrosive, or sterile substances of the type mentioned at the outset, in which the substances to be processed, even when provided only in smallest amounts, are constantly guided past the processing tool during processing and processed.

Another object of the present invention is to provide a device for extracting, fragmenting, mixing, and homogenizing in particularly infectious, malodorous, chemically corrosive, or sterile substances of the above-mentioned type, which allow a simple and malfunction-free removal of the substance processed in the device.

This object is attained in a device having the features of claim 1. Advantageous embodiments of the invention are described in the dependent claims.

The substances unprocessed and being processed are guided past the processing tool by a helically shaped transportation means until the desired consistency is achieved. It is further achieved by a sieve, dividing the processing space in the laboratory test vessel, to separate unnecessary unmilled or to be milled components still contained in the sample to be processed from the optimally homogenized, fragmented, i.e. extracted substances. In a particularly advantageous embodiment of the invention, the removal of these separated materials can occur directly through the hollow shaft of the processing element and, if provided, through a sieve that can be penetrated, without opening the laboratory test vessel. The arrangement of the surface in the sieve that can be penetrated at a tubular or dome-shaped attachment facilitates the penetration of the desired fraction from the processing chamber into the collection chamber.

BRIEF DESCRIPTION OF THE DRAWINGS

Using two illustrated exemplary embodiments the invention is explained in greater detail. Shown are:

FIG. 1 an axial cross-sectional view through a device for processing substances in a laboratory test vessel, FIG. 2 a view of the device from the direction according to arrow P in FIG. 1, FIG. 3 a cross-sectional view through the device taken along a line III-III in FIG. 1, FIG. 4 an enlarged representation of the area A in FIG. 1, FIG. 5 a view of the lid, FIG. 6 an exploded perspective view of the elements used in the laboratory test vessel, FIG. 7 an axial cross-sectional view through the device with a partially inserted pipette, and FIG. 8 an axial cross-sectional view through another embodiment of the device without a guiding function of the laboratory test vessel.

DETAILED DESCRIPTION OF THE PREFERRED EMBODIMENTS

In FIG. 1 the casing of a laboratory test vessel 3 is marked with the reference character 1. The vessel is positioned upside-down, i.e. on the lid 5, with its opening 7 pointing downwards, with the lid sealing the opening 7 of the laboratory test vessel 3. The bottom 9 of the laboratory test vessel 3 is therefore located on the top in these figures. Processing of substances to be extracted, fragmented, mixed, or homogenized occurs in this position. In the following, the term "processing" always characterizes extracting, fragmenting, mixing, and/or homogenizing.

A processing tool 11 is mounted to the lid 5 in a rotation-proof manner. The tool is arranged conically, for example with a multitude of teeth 13. The teeth 13 can be arranged in one or more axially off-set planes in reference to each other. In the illustrated example, the three groups of teeth 13, arranged axially behind each other and showing the form of conical wheels, are arranged on the processing tool 11. The lowermost positioned row of teeth can have a longer distance from the second lowermost row such that at the face a coaxially arranged cutting blade 15 can be placed onto the circular step 17.

The just described part of the processing tool 11 is mounted to the collar 19 of the lid 5, which extends into the interior of the casing 1 of the laboratory test vessel 3. A flange 21 of the lid 5 surrounds the upper brim 23 of the laboratory test vessel 3. Preferably the brim of the lid 5 is provided with a bead 25 pointing inwards, which extends into a recess 27 provided at the upper edge of the casing 1. As an alternative to the just described snap-action lid 5 instead of a bead 25 and recess 27, a thread or a bayonet fitting may be used, of course.

The processing tool 11 comprises a central bore 29 serving as a gliding bearing for a guidance tube 31 of an agitating element 33. At the end facing the lid, this bearing bore 29 is provided with a rib 35 pointing inwardly, which engages an encircling groove 37 at the guidance tube 31 for axially guiding the latter. At the upper end of the bore 29 in the processing tool 11, encircling ribs 39 are formed, facing against the guidance tube 31, which form a labyrinth seal (cf. also the enlarged illustration of the area A in FIG. 4). On the end of the guidance tube 31 facing away from the lid 5, a cap 41 is provided having a, for example, conically extending tip 43. The cap 41 is formed in the area of the tip 43 (the highest area) such that it can be penetrated by the tip of a pipette 45. The tip 43 can either be provided with a predetermined breaking point or may be made from an elastic material penetrable by the pipette tip. Of course, the area that can be penetrated may comprise the same material as the guidance tube 31 and can be produced together with it in a one-component or two-component method. The cap 43 is preferably located, as discernible from FIG. 2, in a plane E inclined in reference to the symmetry axis of the guidance tube 31. The inclined plane E causes materials resting thereupon during processing to automatically glide off and be guided back to the teeth 13.

At the periphery of the agitating element 33, a transportation means 47, made from plastic or metal, extends with a helical form. The interior edge 51 of the transportation means 47 extends in the surface of the casing of a virtual frustum, formed by the edges of the teeth 13. The exterior edge 49 contacts a partial area of the casing 1 of the guidance tube 31. Thus, in the area of the processing tool 11, the interior edge 51 is guided past the crowns of the teeth 13 in a grinding and cutting manner. Therefore, when the agitating element 33 is rotated in the processing tool 11, the transportation means 47 passes over the space between the casing 1 of the laboratory test vessel 3 and the processing tool 11 and/or the cutting blade 15 positioned thereabove. Preferably, slots 53 are provided in the transportation means 47, which can allow the penetration of fluids from the top downwards and together with the cutting blades 15 serve for a coarse fragmenting of the sample.

The rotary drive of the guidance tube 31 and/or the agitating element 33 with the transportation means 47 occurs by an external drive motor, not shown, with its drive shaft engaging through the lid 5 into the interior of the guiding tube 31. The formfitting entraining of the guidance tube 31 is here ensured by cuts 55 arranged at its bore or by fine teeth.

A pin 57 can be placed at the end of the guidance tube 31 facing the lid for transporting the laboratory test vessel 3, in particular after samples were taken, into the lab and/or for additional support. In the embodiment of the invention shown in FIGS. 1-7, a sieve 59 is inserted at the bottom end of the laboratory test vessel 3 and is held in the desired axial position by suitable means 61. The periphery of the sieve 59 contacts the interior wall of the casing 1 in a sealing manner. The sieve 59, as shown in FIG. 3 in an enlarged fashion, may be a perforated plate or it may comprise one or more wire or plastic grids positioned overtop of each other. Within the surface of the sieve a tubular or dome-shaped attachment 63 is provided, which extends beyond the sieve 59 at the side of the lid. A surface 65 that can be penetrated is provided at the attachment 63 above its opening cross-section positioned at the bottom. Preferably, this area 65 is formed conically tapering in a direction towards the sieve 59 and formed such that it can easily be penetrated by the tip of a pipette 45. For this purpose, predetermined breaking points or lines 66 shall be embodied in the area 65, or the area 65 comprises an elastic, easily penetrated membrane. The conically tapering area 65 is positioned coaxially and at a short distance from the tip 43 at the agitating element 33.

In order to increase the effectiveness of the transportation means 47, in the first exemplary embodiment according to FIG. 1, the casing 1 narrows by an angle of 120°, for example, with the upper end of the narrowed section 67 may form a chord 69 in the casing 1. The cross-section of the casing 1 above the chord 69 therefore resembles an arc (cf. FIG. 3).

The base 9 of the laboratory test vessel 3 can be level or bossed or, as shown in FIG. 1, be provided with a sump 71.

The end at the bottom of the lab test housing 3 may also be provided with a collar 75 as a support surface.

In the following the operation of the device is explained.

The completely assembled laboratory test vessel 3 shown in FIG. 1 is opened by removing the lid 5 and then the substance to be processed can be inserted into the interior from the top through the opening 7. The resealed laboratory test vessel 3 with its content is brought to the lab. Now, the laboratory test vessel 3 is brought into the position (lid 5 at the bottom) shown in FIG. 1, and the drive shaft of a motorized drive (not shown) is placed into it. Depending on the rotation of the drive shaft and the processing period, the test substance contained in the laboratory test vessel 3 is now guided over the teeth 13 by the transportation means 47. The transportation means 47 additionally causes the processed substance to be guided constantly in the axial direction within the laboratory test vessel 3 from the bottom upwards and/or from the top downwards to the teeth 13. As soon as the desired fragmenting or homogenization is achieved the operator removes the laboratory test vessel 3 from the drive, turns it such that the lid 5 is on the top. The processed substance can now flow through the sieve 59 into a collection chamber 73. Coarse parts are held back above the sieve 59.

Now, through the hollow guidance tube 31, the pipette 45 can be guided through the cap 41 and from there, guided by the conical area 65, be pierced into the attachment 63. The tip of the pipette 45 is now located in the collection chamber 73 between the bottom of the sieve 59 and the floor 9 of the laboratory test vessel 3. The desired end product of the processing in chamber 73 is therefore free from parts, which could clog the suction opening of the pipette 45. After the sample is taken, a pin 57 can again be placed onto it for storing the remaining homogenized product and thus forming a durable, hermetical seal.

In the simplified embodiment of the invention according to FIG. 8, the agitating element 33 according to the invention and the processing tool 11 are inserted into a cylindrical laboratory test vessel 3. The mixing of the substance being processed again occurs without any particular measures being taken via the transportation means 47 in order to avoid an undesired pushing forward of the sample and to facilitate the overturning of the liquefied material. Additionally, in this embodiment of the invention a sieve is missing, thus there is no holding back of any non-pipettable particles from the processed substance. This embodiment of the invention is suitable for substances containing little or no parts that can be fragmented.

The devices are designed for single use only and are produced preferably entirely from plastic.

The invention claimed is:

1. A device for extracting, fragmenting, mixing, and homogenizing infectious, malodorous, chemically corrosive, or sterile substances, comprising:
    a tubular laboratory test vessel (3) having an open first end and a second end closed by a bottom;
    a closing lid (5) for the laboratory test vessel (3) connected to the open end;
    a processing tool (11) arranged in the closing lid (5) of the laboratory test vessel (3), which is couplable to a drive motor, the processing tool (11) comprises:
        a plurality of teeth (13) mounted to an inside of the closing lid;
        an agitating element (33) having a hollow guidance tube (31) that is rotatably mounted through a central bore (29) in the lid and includes an engagement portion that is adapted to be engaged by the drive motor, with a bottom end thereof being sealed by a cap (41) that is penetratable by a tip of a pipette; and a transportation element (47) arranged on the guidance tube (31) that extends outwardly in a helical shape that extends to the teeth (13) so that upon rotation an interior edge of the transportation element is guided past the teeth in a grinding and cutting manner.

2. A device according to claim 1, wherein a diameter of the transportation element (47) tapers in a direction toward the bottom (9).

3. A device according to claim 1, wherein a conically extending tip (43) is provided in a center of the cap (41).

4. A device according to claim 1, further comprising a sieve (59) that is located in a tubular central part of the laboratory test vessel (3) at a distance from the bottom (9) thereof such that a bottom space is separated from a space at the closing lid.

5. A device according to claim 4, wherein an area (65) that is easily pierceable or penetrable by the tip of the pipette is provided in the sieve (59).

6. A device according to claim 5, wherein a conically extending tip (43) is provided in a center of the cap (41) and is located in the sieve (59) coaxially in reference to the pierceable area (65).

7. A device according to claim 6, wherein the pierceable area (65) in the sieve (59) is arranged at a distance from a surface of the sieve on a tubular or dome-shaped accessory (63) extending towards the opening (7).

8. A device according to claim 5, wherein the pierceable area (65) is provided level or extending conically in a direction of the bottom (9) of the tubular laboratory vessel.

9. A device according to claim 5, wherein the pierceable surface (65) is provided with predetermined breaking points or lines (66) or with an elastic membrane.

10. A device according to claim 2, wherein a base of the tip (43) is arranged on the guidance tube (31) on a surface of the cap located inclined in reference to a symmetry axis (A) of the guidance tube (31).

11. A device according to claim 1, further wherein a casing (1) of the laboratory test vessel (3) is generally arranged to be conically narrowing over an arc ranging from 150 to 180° and a peripheral edge (49) of the transportation element (47) at a conical area of the casing (1) is embodied such that the transportation element can pass thereby.

* * * * *